US010653669B2

(12) United States Patent
Nguyen et al.

(10) Patent No.: US 10,653,669 B2
(45) Date of Patent: May 19, 2020

(54) METHOD FOR PREVENTING AND/OR TREATING AGING-ASSOCIATED COGNITIVE IMPAIRMENT AND NEUROINFLAMMATION

(71) Applicant: THE BOARD OF TRUSTEES OF THE LELAND STANFORD JUNIOR UNIVERSITY, Stanford, CA (US)

(72) Inventors: Khoa Dinh Nguyen, Palo Alto, CA (US); Edgar G. Engleman, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 15/781,756

(22) PCT Filed: Dec. 9, 2016

(86) PCT No.: PCT/US2016/065972
§ 371 (c)(1),
(2) Date: Jun. 6, 2018

(87) PCT Pub. No.: WO2017/106050
PCT Pub. Date: Jun. 22, 2017

(65) Prior Publication Data
US 2018/0353474 A1    Dec. 13, 2018

Related U.S. Application Data

(60) Provisional application No. 62/267,437, filed on Dec. 15, 2015.

(51) Int. Cl.
| *A61K 31/404* | (2006.01) |
| *C07D 235/18* | (2006.01) |
| *A61K 31/4184* | (2006.01) |
| *A61P 25/00* | (2006.01) |
| *A61P 29/00* | (2006.01) |
| *A61K 9/00* | (2006.01) |

(52) U.S. Cl.
CPC .......... *A61K 31/404* (2013.01); *A61K 9/0053* (2013.01); *A61K 31/4184* (2013.01); *A61P 25/00* (2018.01); *A61P 29/00* (2018.01); *C07D 235/18* (2013.01)

(58) Field of Classification Search
CPC ............... A61K 9/0053; A61K 31/404; A61K 31/4184; A61P 25/00; A61P 29/00; C07D 235/18
See application file for complete search history.

(56) References Cited

U.S. PATENT DOCUMENTS

| 4,188,486 A | 2/1980 | Tsukamoto et al. |
| 5,552,426 A | 9/1996 | Lunn et al. |
| 7,781,596 B1 | 8/2010 | Lubisch et al. |
| 9,120,711 B2 | 9/2015 | Nolan et al. |
| 9,233,983 B2 | 1/2016 | Thakkar et al. |
| 2005/0282820 A1 | 12/2005 | Gontcharov et al. |
| 2007/0037865 A1 | 2/2007 | Nunes et al. |
| 2014/0114067 A1 | 4/2014 | Pae et al. |

FOREIGN PATENT DOCUMENTS

| CN | 104873500 A | 9/2015 |
| WO | 8803921 | 6/1988 |
| WO | 2004099190 A1 | 11/2004 |
| WO | 2009127815 A1 | 10/2009 |
| WO | 2016061190 A1 | 4/2016 |

OTHER PUBLICATIONS

Cognitive Disorder, retrieved from https://en.wikepedia.org/w/index.php?title=Cognitive_disorder&oldid=844641350. (Year: 2018).*
International Search Report and Written Opinion issued in PCT/US2016/065972, dated Feb. 17, 2017.
Zhang et al., "Novel Small-Molecule PGC-1 Transcriptional Regulator with Beneficial Effects on Diabetic db/db Mice," Diabetes, 62, pp. 1297-1307 (2013).
Weydt, et al., The gene coding for PCG-1α+-modifies age at onset in Huntington's Disease, Molecular Neurodegeneration, Biomed Central, Ltd., LO, vol. 4, No. 1, p. 3, XP021052334, ISSN: 1750-1326, DOIL 10.1186/1750-1326-4-3 Jan. 8, 2009.
Soyal, et al., A greatly extended PPARGC1A genomic locus encodes several new brain-specific isoforms and influences Huntington disease age of onset+. HumanMolecular Genetics, vol. 21, No. 15, pp. 3461-3473, XP055598439, gb, ISSN: 0964-6906, DOI: 10.1093/hng/dds177 May 15, 2012.
Extended European Search Report issued in PCT/US2016065972 dated Jul. 4, 2019.
Beers, et al., Immune dysregulation in amyotrophic lateral sclerosis: mechanisms and emerging therapies, www.thelancet.com/neurology, vol. 18, pp. 211-220 Feb. 2019.
Wenz, Review Article, Mitochondria and Pgc-1a in Aging and Age-Associated Diseases, Sage-Hindawi Access to Research, Journal of Aging Research, vol. 2011, Article ID 810619, 12 pages, doi:10.4061/2011/810619 Oct. 15, 2010.
Sun, et al., In vitro and in vivo metabolite identification of a novel benzimidazole compound ZLN005 by liquid chromotography/tandem mass spectrometry, Wiley Rapid Communications in Mass Spectrometry, vol. 32, pp. 480-488 Sep. 27, 2017.

(Continued)

*Primary Examiner* — Barbara P Badio

(74) *Attorney, Agent, or Firm* — Heslin Rothenberg Farley & Mesiti, P.C.

(57) ABSTRACT

The present invention is directed to a method for preventing and/or treating aging-related cognitive impairment in the central nervous system. The method comprises administering to a subject in need thereof a Ppargc1a activator 2-(4-tert-butylphenyl)-1H-benzimidazole, 2-[4-(1,1-dimethylethyl)phenyl]-1H-benzimidazole, in an effective amount. A preferred route of administration is oral administration.

3 Claims, 2 Drawing Sheets

(56) References Cited

OTHER PUBLICATIONS

Bottcher, et al., Myeloid cell-based therapies in neurological disorders: How far have we come?, Elsevier, Biochimica et Biophysica Acta, pp. 323-328 2016.
International Search Report issued in PCT/US2015/055479 Jan. 6, 2016.
Benatar, M., Lost in translation: Treatment trials in the SOD1 mouse and in human ALS, Neurobiology of Disease 26:1-13 2007.
DiBernardo, et al., Translating preclinical insights into effective human trials in ALS, Biochimica at Biophysics Acta 1762:1139-1149 2006.
Ernhoefer, et al., Mouse models of Huntington disease: variations on a theme, Disease Models & Mechanisms 2:123-129 2009.
Nazem, et al., Rodent models of neuroinflammation for Alzheimer's disease, Journal of Neuroinflammation 12:74, 15 pages 2015.
Cho, et al., SIRT1 Deficiency in Microglia Contributes to Cognitive Decline in Aging and Neurodegeneration via Epigenetic Regulation of IL-1β Jan. 14, 2015.
International Search Report issued in PCT/US19/45229 Jan. 9, 2020.
Written Opinion of the International Searching Authority issued in PCT/US19/45229 Jan. 9, 2020.
Tert-Butyl 2-phenyl-1H-benzimidazole-1-carboxylate, C18H18N2O2, PubChem available at https://pubchem.ncbi.nim.nih.gov/compound/21863819. Oct. 14, 2019.

\* cited by examiner

METHOD FOR PREVENTING AND/OR TREATING AGING-ASSOCIATED COGNITIVE IMPAIRMENT AND NEUROINFLAMMATION

CROSS REFERENCE TO RELATED APPLICATIONS

This application is a national phase filing under 35 U.S.C. § 371 of PCT International Application PCT/US2016/065972, filed Dec. 9, 2016. PCT/US2016/065972 claimed priority from U.S. Provisional Application No. 62/267,437 filed Dec. 15, 2015. The contents of the prior applications are incorporated by reference herein in their entirety.

FIELD OF THE INVENTION

The present invention relates to methods for preventing and/or treating aging-associated cognitive impairment and neuroinflammation by administering to a subject a Ppargc1a activator 2-(4-tert-butylphenyl)-1H-benzimidazole, 2-[4-(1,1-dimethylethyl)phenyl]-1H-benzimidazole.

BACKGROUND

Microglia are immune cells that are located only in the CNS. Microglia originate from a yolk-sac hematopoietic progenitor, which populates the brain during embryogenesis (Ginhoux et al Science 2009). During homeostatic conditions, microglia carry out reparative processes such as debris clearance. They also produce an arsenal of inflammatory mediators, which could be released upon receiving pathological stimuli, to initiate and sustain neuroinflammation. Similar to other immune cells, microglial activation is a bio-energetically demanding process. What currently remains elusive is how microglial metabolism becomes maladaptive and contributes to the inflammatory transformation of these cells.

Inflammatory responses in the brain, which can be demonstrated by the presence of pro-inflammatory molecules and changes in the properties of microglia, are a common feature of human neurodegenerative diseases (Alzheimer's Res Ther., 7(1):56. doi: 10.1186/s13195-015-0139-9, 2015). Yong (The Neuroscientist, 16:408-420, 2010) reports that inflammation of the central nervous system (CNS) (neuroinflammation) is a feature of all neurological disorders, and microglia activation results in elevation of many inflammatory mediators within the CNS.

Aging is associated with a progressive loss of tissue function, resulting in an increased susceptibility to aging-related disorders. A consequence of physiological aging is a greater susceptibility to memory impairment following an immune challenge such as infection, surgery, or traumatic brain injury. The neuroinflammatory response, produced by these challenges, results in increased and sustained production of pro-inflammatory cytokines in the otherwise healthy aging brain. Sensitized microglia are a primary source of this exaggerated neuroinflammatory response and appear to be a hallmark of the aging brain. The causes and effects of aging-induced microglial sensitization include dysregulation of the neuroendocrine system, potentiation of neuroinflammatory responses following an immune challenge, and the impairment of memory (Barrientos et al, Neuroscience 309:84-99, 2015). Aging is associated with a decline in cognitive performance, and is the biggest risk factor for the development of Alzheimer's disease (AD). Mosher et al (Biochem Pharmacol 88:594-604, 2014) report microglial dysfunction in brain aging and Alzheimer's disease. Nevertheless, the role of intrinsic regulatory pathways in microglia in these phenomena remains unexplored.

Since the population of aging individuals is rapidly expanding and neuroinflammation is a pro-longed process that develops during mid-life (40-60 years old) and accelerates with old age (over 60 years old), it is important to identify a novel therapeutic target for treating as well as preventing aging-related disorders. There is a need for a therapy to inhibit microglia-mediated neuroinflammation and its pathological consequences in aging.

BRIEF DESCRIPTION OF THE DRAWINGS

FIG. 1 shows % of microglia that either express glucose transporter Slc2a1 or have taken up glucose fluorescent analog 2-NBDG in young animal, vehicle-treated older animals, or ZLN-treated older animals; n=6 animals per condition.

FIG. 2 shows % of microglia that express CCL2 or TNF-α in young animals, vehicle-treated older animals, or ZLN-treated older animals; n=6 animals per condition.

FIG. 3 shows the concentration of TNF-α in serum of young animals, vehicle-treated older animals, or ZLN-treated older animals; n=6 animals per condition.

FIG. 4 shows the marble burying score in young animal, vehicle-treated older animals, or ZLN-treated older animals; n=8-9 animals per condition.

DETAILED DESCRIPTION OF THE INVENTION

Figure 1:
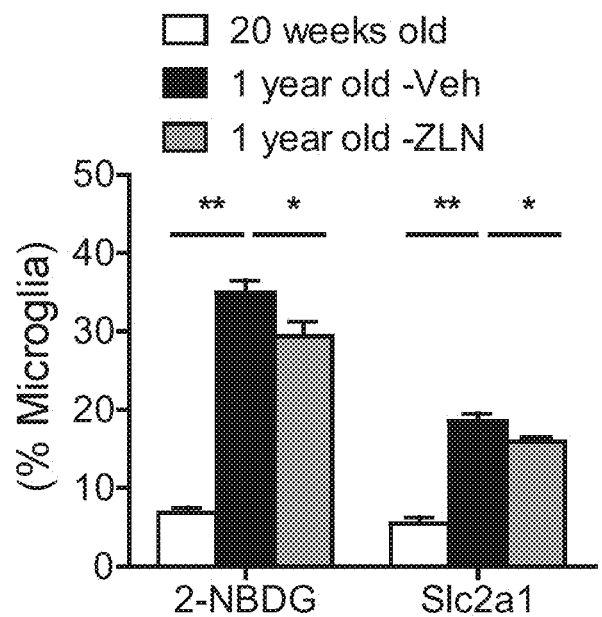
In FIGS. 1-4, Veh=0.5% methylcellulose oral gavage, ZLN=ZLN005 in Veh.

The inventors have discovered that Ppargc1a, a pleotropic regulator of cellular metabolism in many cell types including microglia, is an important regulator of aging-associated neuropathic disorders. The inventors have discovered a connection between Ppargc1 activation in microglia and its effect on the cognitive and motor functions of the whole organism. The inventors have discovered that activating Ppargc1a with compounds such as ZLN005 ameliorates microglial dysfunction and improves cognitive performance in older animals.

The present invention is directed to a method for preventing or treating age-associated cognitive impairment or neuroinflammation. The method comprises the step of administering a Ppargc1a activator to a subject in need thereof, in an amount effective to prevent, arrest, or reverse the development of aging-related symptoms. "Preventing," as used herein, refers to arresting or slowing progression of age-associated cognitive impairment or neuroinflammation. "Treating," as used herein, refers to reverse, alleviate, or reduce age-associated cognitive dysfunction or neuroinflammation. The subject is an aging subject (45-60 years old) or an old subject (over 60 years old).

2-(4-tert-Butylphenyl)-1H-benzimidazole, 2-[4-(1,1-Dimethylethyl)phenyl]-1H-benzimidazole, CAS Number 49671-76-3, also known as ZLN005, is an effective Ppargc1a activator useful for treating aging. The chemical structure of ZLN005 is shown below.

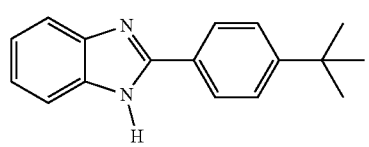 [SMILES: CC(C)(C)c1ccc(-c2nc3ccccc3[nH]2)cc1]

The inventors have demonstrated that microglia in older mice are more glycolytic, evidenced by their increased utilization of glucose as its energy substrate and an upregulation of the glucose transporter Slc2a1. Treating these older animals with ZLN005 led to a significant inhibition of glucose uptake as well as Slc2a1 expression in microglia.

The inventors have shown that microglia in older mice exhibit an inflammatory phenotype, evidenced by a significant increase in CCL2 and TNF-α production. Tumor necrosis factor (TNF or TNFα) is a cell signaling protein (cytokine) involved in local and systemic inflammation and is one of the cytokines that make up an acute phase reaction. The chemokine (C—C motif) ligand 2 (CCL2) is a small cytokine, which recruits monocytes, memory T cells, and dendritic cells to the sites of inflammation produced by either tissue injury or infection. By administering ZLN005 to older animals, CCL2 and TNF-α production in microglia decreased and neuroinflammation was suppressed. In addition, ZLN005 treatment suppressed systemic inflammation in older mice, evidenced by its inhibitory effect on serum TNF-α level.

The inventors have provided evidence that treatment with ZLN005 reduced or reversed behavioral dysfunction, i.e., cognitive dysfunction, in older mice in a marble-burying test, which is a functional assay to assess cognitive competency.

Pharmaceutical Compositions

The present invention provides pharmaceutical compositions comprising one or more pharmaceutically acceptable carriers and an active compound of 2-(4-tert-butylphenyl)-1H-benzimidazole, 2-[4-(1,1-dimethylethyl)phenyl]-1H-benzimidazole (ZLN005), or a pharmaceutically acceptable salt, or a solvate thereof. The active compound or its pharmaceutically acceptable salt or solvate in the pharmaceutical compositions in general is in an amount of about 0.01-20% (w/w) for a topical formulation; about 0.1-5% for an injectable formulation, 0.1-5% for a patch formulation, about 1-90% for a tablet formulation, and 1-100% for a capsule formulation.

In one embodiment, the pharmaceutical composition can be in a dosage form such as tablets, capsules, granules, fine granules, powders, syrups, suppositories, injectable solutions, patches, or the like. In another embodiment, the pharmaceutical composition can be an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

In another embodiment, the active compound is incorporated into any acceptable carrier, including creams, gels, lotions or other types of suspensions that can stabilize the active compound and deliver it to the affected area by topical applications. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfate, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Binders promote the adhesion of particles of the formulation and are important for a tablet formulation. Examples of excipients of a tablet or a capsule include, but are not limited to, carboxymethylcellulose, cellulose, ethylcellulose, hydroxypropylmethylcellulose, methylcellulose, karaya gum, starch, tragacanth gum, gelatin, magnesium stearate, titanium dioxide, poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and/or titanium dioxide. A capsule formulation may contain inactive ingredients such as gelatin, magnesium stearate, and/or titanium dioxide.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

Method of Use

The present invention is directed to a method of preventing and/or treating aging-related cognitive impairment and/or neuroinflammation. The method prevents aging-related cognitive impairment and neuroinflammation of the central nervous system and/or reduces or reverses these symptoms once developed. The method comprises the steps of first identifying a subject in need thereof, and administering to the subject the active compound of ZLN005, in an amount effective to treat aging-related symptoms. "An effective amount," as used herein, is an amount effective to treat an aging-related condition by reducing its symptoms.

In one embodiment, the method reverses or reduces behavioral dysfunctions in an older or aging patient. In one embodiment, the method suppresses neuroinflammation as well as systemic inflammation of the subject. In one embodiment, the method suppresses metabolic abnormalities of microglia in the brain of the subject.

The pharmaceutical composition of the present invention can be applied by local administration and systemic administration. Local administration includes topical administration. Systemic administration includes, but not limited to oral, parenteral (such as intravenous, intramuscular, subcutaneous or rectal), and inhaled administration. By systemic administration, the active compound first reaches plasma and then distributes into target tissues. Oral administration is a preferred route of administration for the present invention.

Dosing of the composition can vary based on the extent of the injury and each patient's individual response. For systemic administration, plasma concentrations of the active compound delivered can vary; but are generally $1 \times 10{-}10$-$1 \times 10{-}4$ moles/liter, and preferably $1 \times 10{-}8$-$1 \times 10{-}5$ moles/liter.

In one embodiment, the pharmaceutical composition is administrated orally to the subject. The dosage for oral administration is generally 1-100, and preferably 1-50, or 1-25 mg/kg/day. For example, the active compound can be applied orally to an adult human at 50-1000 mg/dosage, or 100-600 mg/dosage, 1-4 times a day, depends on the patient's condition and weight.

In one embodiment, the pharmaceutical composition is administrated subcutaneously to the subject. The dosage for subcutaneous administration is generally 0.3-20, and preferably 0.3-3 mg/kg/day.

In one embodiment, the composition is applied topically onto the affected area and rubbed into it. The composition is topically applied at least 1 or 2 times a day, or 3 to 4 times per day, depending on the medical issue and the disease pathology. In general, the topical composition comprises about 0.01-20%, or 0.05-20%, or 0.1-20%, or 0.2-15%, 0.5-10, or 1-5% (w/w) of the active compound. Typically 0.2-10 mL of the topical composition is applied to the individual per dose. The active compound passes through skin and is delivered to the site of discomfort.

Those of skill in the art will recognize that a wide variety of delivery mechanisms are also suitable for the present invention.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

EXAMPLES

All animal studies were conducted under protocols approved by APLAC from Stanford University. Older and young animals on C57BL6 background were purchased from Taconic. Older animals are defined as those above 36 weeks of age, when physiological aging process accelerates in mice, while young counterparts are 20 weeks of age. Data are presented as mean±SEM. Two-tailed Student's t-test and two-way ANOVA were used for statistical analyses. A p value of <0.05 is considered to be statistically significant.

Example 1. Ppargc1a Activator ZLN005 Suppresses Metabolic Dysfunction in Microglia in Older Mice Older animals were orally treated 3 times a week for 15 weeks with 0.5% methylcellulose (vehicle) or ZLN005 (Sigma) at 25 mg/kg in vehicle, starting at 37 weeks of age. Treated older animals (n=6), non-treated older animals (n=6), and young animals (20 weeks old, n=6) were sacrificed after drug treatment and their brain tissues collected. PBS-perfused brain tissues of sacrificed animals were digested with Collagenase I and processed for flow cytometry (Ginhoux et al Science, 330:841-5, 2010). Brain microglia were phenotyped with 2-NBDG (2-(N-(7-nitrobenz-2-oxa-1,3-diazol-4-yl)amino)-2-deoxyglucose, Invitrogen) and anti-Slc2a1 antibody (RnD) for flow cytometric acquisition (LSRII, BD) and analysis (FlowJo).

The results are summarized in FIG. 1; Y-axis represents % of microglia that either express glucose transporter Slc2a1 or have taken up glucose fluorescent analog 2-NBDG. ANOVA was used for statistical analysis. The results show that microglia in older mice exhibited a glycolytic activation phenotype, evidenced by a significant increase in Slc2a1 expression as well as 2-NBDG uptake in vehicle treated older mice when compared with young mice (p-values <0.01). The results also show that by administering ZLN005 to older animals, Slc2a1 expression and glucose uptake in microglia of these treated animals decreased, and thus their metabolic dysfunctions were alleviated. (p-values <0.05).

Example 2. Ppargc1a Activator ZLN005 Inhibits Inflammatory Cytokine Production in Microglia in Older Mice Older animals were orally treated 3 times a week for 15 weeks with 0.5% methylcellulose (vehicle) or ZLN005 (Sigma) at 25 mg/kg in vehicle, starting at 37 weeks of age. Treated older animals (n=6), non-treated older animals or aged animals (n=6), and young animals (20 weeks old, n=6) were sacrificed after drug treatment and their brain tissues were collected. PBS-perfused brain tissues of sacrificed animals were digested with Collagenase I and processed for flow cytometry (Ginhoux et al Science, 330:841-5, 2010). Brain microglia were phenotyped with fluorochrome-labeled antibodies to CCL2 and TNF-α (Biolegend) for flow cytometric acquisition (LSRII, BD) and analysis (FlowJo).

Figure 2:
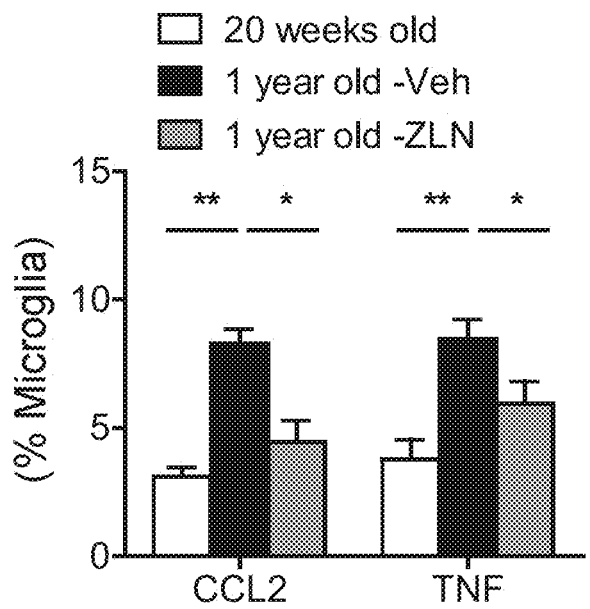

The results are summarized in FIG. 2; Y-axis represents % of microglia that express CCL2 or TNF-α. ANOVA was used for statistical analysis. The results show that microglia in older mice exhibited an inflammatory phenotype, evidenced by a significant increase in CCL2 and TNF-α production in vehicle-treated older mice when compared with young mice. The results also show that by administering ZLN005 to older animals, CCL2 and TNF-α production in microglia of these treated, older animals decreased and thus neuroinflammation was suppressed (p-values <0.05 for TNF-α and <0.01 for CCL2).

Figure 3:
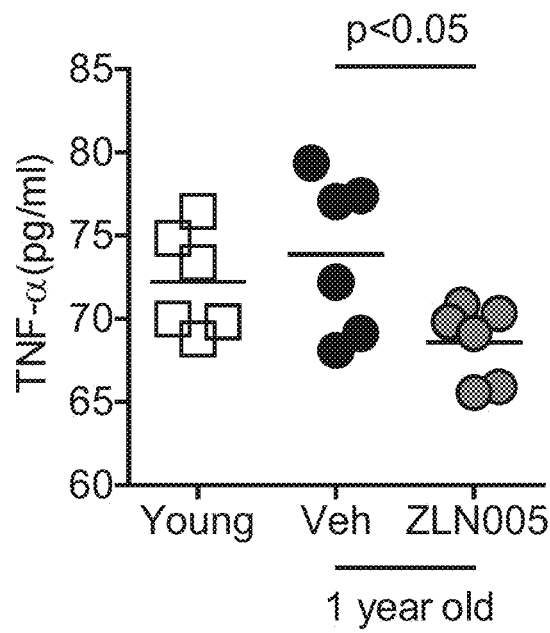

Example 3. Ppargc1a Activator ZLN005 Suppresses Systemic Inflammation in Older Mice TNF-α levels in serum of young mice, vehicle-treated older mice, and ZLN-treated older mice (from Example 2)

were measured by ELISA to determine TNF-α levels which indicated systemic inflammation. The results are summarized in FIG. 3; Y-axis represents the concentration of TNF-α in serum. The results show that by administering ZLN005 to older animals, TNF-α levels in serum of these treated and older animals decreased and thus systemic inflammation was suppressed when compared with vehicle-treated older animal (p-value <0.05). Unpaired t-test was used for statistical analysis.

Figure 4:
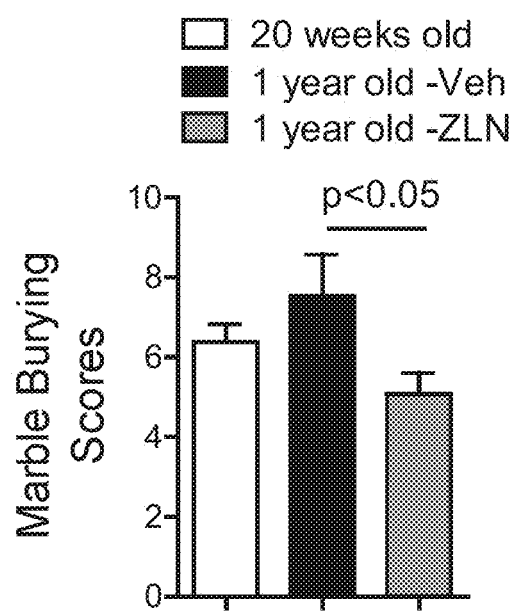

Example 4. Ppargc1a Activator ZLN005 Alleviates Behavioral Dysfunction in Older Mice Animals were orally treated 3 times a week for 15 weeks with 0.5% methylcellulose (vehicle) or ZLN005 (Sigma) at 25 mg/kg in vehicle, starting at 37 weeks of age. At 52 weeks of age, the older animals were subjected to a marble burying assay, a behavioral test of anxiety (Dekeyne A, Therapie, 60:477-84, 2005). Each animal was given 12 marbles on top of bedding in individual cage and allowed to run free in the cage for 30 minutes. After this period of time, each buried marble was individually assigned a number based on its degree of being buried (1=90-100% hidden, 0.75=60-90% hidden, 0.5=30-60% hidden, 0=below 30% hidden), and then the sum of the numbers of 12 marbles buried by each mouse is calculated as the marble burying score of the mouse. The higher score an animal had, the higher anxiety index it exhibited. Results in FIG. 4 reveal that older mice treated with vehicle had a higher average score than those treated with ZLN005 (p-value <0.05), indicating that ZLN005 reduced the anxiety phenotype and corrected behavioral dysfunction in older mice (n=8-9 mice per group). Unpaired t-test was used for statistical analysis.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method of slowing the progression of or alleviating cognitive impairment in persons over the age of 40, comprising the step of: administering to a subject in need thereof an effective amount of 2-[4-(1,1-dimethylethyl)phenyl]-1H-benzimidazole, or a pharmaceutically acceptable salt thereof.

2. The method according to claim 1, wherein said compound is administered by systemic administration.

3. The method according to claim 1, wherein said compound is administered by oral administration.

* * * * *